US008115931B2

(12) United States Patent
Miklos et al.

(10) Patent No.: US 8,115,931 B2
(45) Date of Patent: Feb. 14, 2012

(54) PHOTOACOUSTIC DETECTOR FOR MEASURING FINE DUST

(75) Inventors: Andras Miklos, Stuttgart (DE); Judit Angster, Stuttgart (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 84 days.

(21) Appl. No.: 12/593,163

(22) PCT Filed: Mar. 27, 2008

(86) PCT No.: PCT/EP2008/002432
§ 371 (c)(1),
(2), (4) Date: Sep. 25, 2009

(87) PCT Pub. No.: WO2008/116655
PCT Pub. Date: Oct. 2, 2008

(65) Prior Publication Data
US 2010/0103425 A1  Apr. 29, 2010

(30) Foreign Application Priority Data

Mar. 27, 2007  (DE) .................. 10 2007 014 519

(51) Int. Cl.
*G01N 21/00*  (2006.01)
(52) U.S. Cl. .......... 356/438; 73/24.03; 422/73; 356/336
(58) Field of Classification Search .................. 356/438, 356/440, 336; 73/24.02, 61.75, 24.03
See application file for complete search history.

(56) References Cited

U.S. PATENT DOCUMENTS

| | | | | |
|---|---|---|---|---|
| 4,212,190 A * | 7/1980 | Coover et al. | ................ | 73/24.03 |
| 4,722,602 A | 2/1988 | Kitamori et al. | | |
| 4,827,144 A * | 5/1989 | Zaitsu et al. | .................. | 250/574 |
| 5,178,836 A | 1/1993 | Kitamori et al. | | |
| 6,662,627 B2 * | 12/2003 | Arnott et al. | ................. | 73/24.02 |
| 6,748,815 B2 * | 6/2004 | Povey et al. | ................. | 73/865.5 |
| 7,567,596 B2 * | 7/2009 | Dantus et al. | ................... | 372/30 |
| 2006/0290944 A1 | 12/2006 | Arnott et al. | | |
| 2009/0038375 A1 | 2/2009 | Breuer et al. | | |
| 2010/0107732 A1 | 5/2010 | Miklos et al. | | |
| 2010/0107733 A1 | 5/2010 | Miklos et al. | | |

FOREIGN PATENT DOCUMENTS

| | | |
|---|---|---|
| DE | 102005030151 | 11/2006 |
| EP | 0213468 | 3/1987 |
| JP | 59126933 | 7/1984 |

OTHER PUBLICATIONS

A. Petzold, R. Niessner "Photoacoustic sensor for carbon aerosols." vol. B14 pp. 640-641. 1993.

(Continued)

*Primary Examiner* — Tarifur Chowdhury
*Assistant Examiner* — Isiaka Akanbi
(74) *Attorney, Agent, or Firm* — Greenblum & Bernstein, P.L.C.

(57) ABSTRACT

A photoacoustic detector for measuring a concentration of fine dust particles in gas. The detector includes at least one acoustic sensor for detecting an acoustic signal. Additionally, the detector includes a pulsed light source for providing excitation light having a configurable pulse length and a configurable pulse repetition rate, wherein by changing the pulse length and/or the pulse repetition rate, a size distribution of the fine dust particles can be determined.

20 Claims, 1 Drawing Sheet

OTHER PUBLICATIONS

K.P. Guton et al. "In situ infrared aerosol spectroscopy for a variety of nerve agent simulants using flow-through photoacoustics." Applied Optics, vol. 46, No. 25 (Jun. 26, 2007).

Belton P S et al. "Quantitative Analysis of Fourier Transform Infrared Spectroscopy", vol. 917 p. 72-77, 19000101, Jan. 1, 1900, XP008093727.

German Search Report and/or Written Opinion and a partial English-language translation of the corresponding German Search Report and/or Written Opinion for corresponding application 10 2007 014 519.

English-language International Preliminary Report on Patentability for PCT/EP2008/002432.

* cited by examiner

US 8,115,931 B2

PHOTOACOUSTIC DETECTOR FOR MEASURING FINE DUST

CROSS REFERENCE TO RELATED APPLICATIONS

The present application is a U.S. National Stage of International Application No. PCT/EP2008/002432 filed Mar. 27, 2008, which published as WO 2008/116655 A1 on Oct. 2, 2008, the disclosure of which is expressly incorporated by reference herein in its entirety. Further, this application claims priority under 35 U.S.C. §119 and §365 of German Application No. 10 2007 014 519.7 filed Mar. 27, 2007.

BACKGROUND OF THE INVENTION

1. Field of the Invention

The invention relates to a photoacoustic detector for measuring fine dust in gas.

2. Background Description

Photoacoustic measuring methods, i.e., measuring methods in which the substance being tested, preferably a gas or a solid object surrounded by a gas, is irradiated by a light source and heated by absorption, are well suited for precise measurements of the concentration of absorbing substances. The heating produces an expansion of the surrounding gas. If the heating, and thus, the expansion take place periodically, a sound wave is generated, which can be measured by a sound pressure sensor.

The measurement of fine dust in the air has played a role for years in the monitoring of air quality. In addition, efforts are also being made to determine the fine dust content of exhaust gases, wherein in particular the content of soot particles is of interest. Photoacoustic measuring methods have been known for this purpose for some time. Due to the increased expense in terms of equipment, however, they have not gained acceptance in the past. Possibly playing a role in this connection is that, in the monitoring the ambient air, as a rule average values over longer periods of time, for instance, averages over a half hour or an hour, are needed. It lends itself here to guide the air through a filter and measure the clogging thereof. The possibilities for automation are limited, however. In the case of the adjustment and inspection of combustion engines, for example, current values, rather than longer average values, are of interest. Of crucial interest in the measurement of fine dust particles is also the size of the fine dust particles. The size of the fine dust particles is of crucial importance in their harmful effect on health.

The suitability of the photoacoustic effect for measuring fine dust particles has already been proven by scientific studies by A. Petzold, R. Niessner "Photoacoustic sensor for carbon aerosols." Corresponding devices can also be acquired commercially, for instance, AVL Micro Soot Sensor, http://www.avl.com. However, the size of the fine dust particles cannot be determined therewith.

Determining particle sizes in a liquid with the aid of a photoacoustic measurement is known from U.S. Pat. No. 4,722,602. The photoacoustic pulse produced is used for this purpose.

Inferring the size of particles, preferably particles in liquids, from the amplitude of the generated acoustic wave is known from U.S. Pat. No. 5,178,836.

Determining the size of particles in a liquid photoacoustically from the intensity and the phase shift is known from JP 59126933.

SUMMARY OF THE INVENTION

The aim of the present invention is therefore to develop a detector, which renders possible time-resolved and, in particular, size-resolved measurements of fine dust particle concentrations in the air. In particular, a measurement in exhaust gas should also be possible.

This aim is attained by the device and the method which are disclosed in the independent claims. The dependent claims disclose advantageous further developments.

It was recognized that a photoacoustic detector for measuring fine dust in gas with a pulsed light source for providing excitation light, in which by changing the pulse length and/or the pulse repetition rate a size distribution of the fine dust particles can be determined, attains the aforementioned aim. In this case, the different thermal capacity of larger and smaller fine dust particles is used. The larger in size a particle is, the greater its mass and its thermal capacity as well. In the case of an excitation with a light pulse (which are normally laser pulses), the particles are first heated by absorption of light. Then the particles emit heat to the environment. The heating of the surrounding gas then leads to an expansion, which causes a pressure wave that is measurable as sound. Because of the cross section, and thus, the larger absorption surface, more light is absorbed in the larger particles and thus more heat is absorbed. Since the effectively absorbing surface increases approximately with the square of the diameter, but the thermal capacity, which is proportional to the mass, increases with the cube of the diameter, there is a smaller increase in temperature in the case of larger particles. Overall, however, as explained, more heat is stored in the larger particles. It takes longer than with smaller particles until this heat is emitted to the environment. The time difference between the duration of the exciting pulse and the duration of the photoacoustic signal is thus greater with larger particles than with smaller particles. In the case of an increase in the pulse duration, all particles are heated more strongly. As a result, a size distribution can be inferred from comparing several photoacoustic signals with different light pulse lengths. This effect can be determined and shown by numerical calculation. In practice it is always advantageous, however, to calibrate the respective detector by measuring reference samples.

The size distribution of the fine dust particles can also be determined by changing the pulse repetition rate. As explained, the particles are heated with every pulse and subsequently emit their heat to the environment. In the process, smaller particles cool down more between the individual excitation pulses than larger particles. Since only the respective temperature change of the ambient air contributes to the photoacoustic signal, the photoacoustic signal is greater if the absorbed heat is emitted as completely as possible to the environment between the individual excitation pulses. If the pulse repetition rate is increased, the larger particles are thus not able to adequately emit their heat to the ambient air between the individual excitation pulses and therefore contribute less to the photoacoustic signal. As a result, the size distribution of the detected fine dust particles can be inferred from a comparison of the overall photoacoustic signal with larger and smaller pulse repetition rates. This can also be shown by numerical calculation. To achieve more precise measuring results, it is advantageous, however, to calibrate the detector with known samples.

The informative value of fine dust particle measurements can therewith be increased in a relatively simple manner, since an indication of the size distribution of the particles is obtained along with information about the concentration. As mentioned at the outset, the adverse health effects of the fine dust particles are dependent upon their size. Furthermore, different particle sizes can also provide information about the source or the cause of the fine dust contamination.

In a further development, a detection of the excitation light scattered by the fine dust is also possible. As a result, it is possible to differentiate whether the photoacoustic signal originates from absorbing gases, which do not scatter the light, or from scattering particles. Furthermore, the scattered light measurement makes it possible to determine in more detail the type of the fine dust. Thus, in the case of highly absorbing soot, the photoacoustic signal is greater in comparison to the scattered light signal than, for instance, in the case of low absorbing sand particles or dust particles. Because the composition of the fine dust is of importance with respect to the adverse health effects, this additional information is advantageous.

In order to increase the measuring sensitivity, it is advantageous to provide an optical multi-pass arrangement and an arrangement for the concentration of the acoustic energy. In general, this offers an advantage because the requirements for the sensitivity of the sound pressure sensor can be limited. In this case, it is significant that, through a suitable concentration, above all the signal, and less so the background noises, can be concentrated. Interference signals are reduced therewith. In particular in the case of measurements in exhaust gas, the problem can arise that the sound pressure sensors cannot withstand the high temperatures prevailing there. In order to avoid an arrangement of the sound pressure sensors in the area of the hot gas, the concentration can be accomplished such that the area of the maximum sound pressure lies in an area in which the temperature is lower than in the gas being tested. Thus, for instance, the acoustic energy can be guided out of an exhaust gas flow and a maximum concentration of the sound pressure can be achieved outside the hot exhaust gas flow.

If reflectors are used for the concentration of the acoustic energy, which can also be used for the concentration of the scattered excitation light, then the number of attachments incurring costs and requiring maintenance can be reduced. In addition, it is frequently useful in any case to concentrate the sound pressure and the scattered excitation light in similar areas.

In a preferred embodiment, it is possible to measure the fine dust particles in a gas flowing through the detector. As a result, for instance, exhaust gas can be directed through the detector without a laborious sample preparation being required. In addition, continuous measurements can take place, for instance, in exhaust gas systems or ventilation systems.

Occasionally, the concentration of the sound pressure and/or of the scattered excitation light in an area in which there is a lower temperature can be difficult. A high temperature can also still exist in these areas. For this reason, it is advantageous if a cooling device is present for sensors that can detect the sound pressure, and/or for sensors that can detect the scattered light. Water cooling can be provided here. A local cooling through Peltier elements can also reduce the thermal stress of the sensors.

A further possibility for reducing the thermal stress of sensors is providing a thermal decoupling between the region of the production and the detection of the acoustic signal. Different possibilities are conceivable here.

It is especially favorable to guarantee the thermal decoupling by a sound-permeable and/or transparent film, which is embodied to be thermally insulating. For example, a film made of polyimide meets the aforementioned requirements.

A rugged and temperature-resistant device for detecting the acoustic signal is an optical microphone. In the case of an embodiment of an optical microphone, the light, for instance, a light-emitting diode, is conveyed through a lens array via an optical fiber. As a result, the light beam is directed onto a reflective membrane. If the membrane now oscillates, as it does with excitation by sound, the light signal changes. A remote photodetector, i.e., not arranged in the area of high temperature, converts the light signal into electrical voltages. Thus, a detector can be set up in the area of normal temperatures. Merely the aforementioned optical elements need to withstand the high temperatures. Microphones of this type have been known for some time and are increasingly available at a low price.

A favorable arrangement of the sensors for detecting the acoustic signal and for detecting the optical signal is produced in that the sensors are arranged close together in such a way that with a common concentration of the acoustic energy and of the scattered light, both sensors are arranged in the region of the maximum signal. Thereby, understandably, the area of the maximum signal should not be understood to be the exact point of the local maximum of the sound pressure or of the scattered excitation light. This is merely an area in which a very high signal is present so that it is possible to refer to an area of the maximal signal. It is also possible to refer to an area of the maximal signal in the case of signals up to 20% below the local maximum.

In order to be able to carry out a measurement with different wavelengths, and thus, to achieve a better differentiation between carbon particles and conventional dust particles, it is useful if at least three diode lasers are present for providing the excitation light.

An increase of the photoacoustic signal as well as of the scattered light signal is produced, if the excitation light can be guided multiple times through the measuring area. This can be accomplished by correspondingly reflecting elements. Light transit times are relatively short in comparison to the times of the acoustic signal generation, i.e., the time that is required to correspondingly heat the gas and be able to detect the resulting sound pressure signal. The light transit times are also short in comparison to the pulse durations or to the time intervals between the pulses. A multiple guiding of the excitation light through the measuring area does therefore not impede determining the size distribution of the fine dust particles through changing the pulse length or pulse repetition rate.

One possibility of achieving a high photoacoustic signal is yielded by providing a cylindrical acoustic resonator, which has an arrangement to guide the excitation light such that the sound wave that can be excited by absorption of the excitation light is the second azimuthal resonance of the cylinder oscillation. In this manner, a resonance effect is used which increases the acoustic signal. A cylindrical resonator also offers a suitable geometry so that the gas to be measured can flow favorably through the detector.

In order to realize the amplification of the signal, a cylinder is observed in cross section. If suitable excitation is used to achieve expansions in opposing areas of the circle that represents the cylinder cross section, while no expansion occurs in the areas adjacent to the opposing areas, which again lie opposite one another, a corresponding sound wave is obtained. Through the excitation, circle segments thereby form with a pressure increased by the expansion. The adjacent circle segments, which are larger, do not have an increased pressure, but normal pressure. Due to this difference in pressure, a sound wave circulating in a cylinder can form. Through a suitable selection of the excitation frequency, i.e., the repetition frequency or modulation frequency of the light source, the second azimuthal resonance can be excited. As a result, a high amplification of the photoacoustic signal occurs.

A suitable arrangement for guiding the excitation light constitutes four mirrors, which are arranged lying oppositely in groups of respectively two mirrors in the cylindrical acoustic resonator. In this way, the light can strike a first mirror and be reflected from there onto a second mirror lying opposite. This reflects the light to an adjacent third mirror. From here the reflection goes to a fourth mirror lying opposite the third mirror. This fourth mirror finally directs the light again to the first mirror, which is adjacent to it. An increase in the sound pressure is therewith achieved in opposing areas of the cylinder. This can produce an azimuthal oscillation in the cylinder. If the excitation frequencies are selected accordingly, an azimuthal oscillation develops with the second azimuthal resonance of the cylinder oscillation.

An alternative embodiment of the detector is produced, if the detector features an acoustically open measuring area that is not completely surrounded by a housing. This detector contains an arrangement for introducing excitation light into the measuring area so that the excitation light can be absorbed by fine dust particles located in the measuring area to produce acoustic energy. In addition, at least one acoustic sensor is to be provided, wherein an arrangement is present to achieve a local maximum of the sound pressure at least one position. The at least one acoustic sensor is arranged in the vicinity of the at least one position at which the local maximum of the sound pressure produced is present. Details can be found in DE 10 2005 030 151, which is herewith incorporated in the disclosure of the present application.

Acoustic mirrors, in particular parabolic acoustic mirrors, are a suitable possibility for producing a local maximum of the sound pressure.

Of special importance is a measuring device for the time-resolved measurement of the exhaust gas of a motor vehicle or of an engine test bench with a photoacoustic detector according to one of the preceding claims. In the inspection, and even more, in the development of engines, it is not sufficient if complicated measuring techniques are available with which a delayed analysis of the signal is possible. Rather, it is desirable if real-time information can be provided concerning the exhaust gas contamination. Adjustments can thus be made with which the exhaust gas contamination can be reduced. With the present invention, it is possible to create measuring devices which can be procured by workshops at a reasonable price. As a result, an adjustment of the engine can take place at regular maintenance intervals of motor vehicles in such a manner that the impact can be reduced from fine dust particles harmful to health.

BRIEF DESCRIPTION OF THE DRAWING

Without restricting the generality, the invention is described in greater detail below on the basis of an exemplary embodiment. In this case.

DETAILED DESCRIPTION OF THE INVENTION

Figure 1:
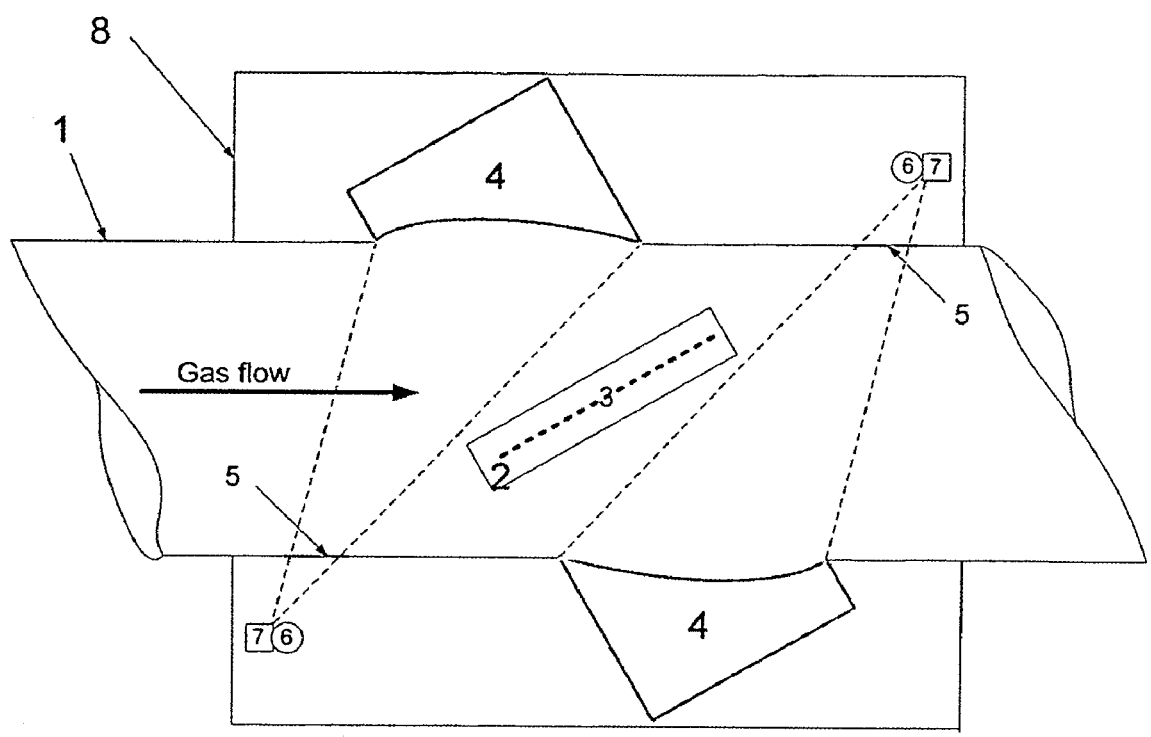
FIG. 1 shows a measuring apparatus for measuring in hot exhaust gas.

The main portion of the photoacoustic fine dust detector is a pipe 1 made of metal or ceramic the diameter of which is coordinated such that it is possible to install it in an exhaust gas pipe. The measuring attachments are enclosed in an annular housing 8. Located in the pipe 1 are two pairs of gold-coated optical mirrors. On the one hand, two planar mirrors 2 are arranged, of which only the upper one is visible in the drawing. These planar mirrors serve to guide the light coming from a laser source (not depicted in the FIGURE) via reflections multiple times through the measuring area. In the process, the light beam is not always reflected at the same location of the mirror. Instead, the incidence point of the light migrates a little bit further in each case from reflection to reflection. As a result, a line of incidence points 3 emerges. The fine dust particles absorb the light from the laser pulse. Moreover, the light is scattered on the fine dust particles. Through the absorption and the subsequent heating of the surrounding air, a photoacoustic signal is produced. Furthermore, a scattered light signal is produced. In the other pair of mirrors, a pair of concave mirrors 4 that are 60° off-axis, the photoacoustically produced sound waves as well as the scattered light are reflected in focal points.

Located in the area of the focal points are acoustic ultrasonic sensors (or detectors) 6 and optical detectors 7, which are located outside the pipe 1. Openings are contained in the pipe 1, through which openings the sound waves concentrated by the concave mirrors 4 and the scattered light concentrated by the concave mirrors can reach the detectors. Located in these openings is a thin heat-resistant plastic film 5 made of polyimide. Because of this film 5, the temperature of the hot exhaust gas flowing through the pipe 1 does not reach the detectors 6, 7. As a result, less expensive detectors can be used. To accommodate the concave mirrors 4 and the detectors 6, 7 there is an annular housing, which surrounds the pipe. Because the detectors 6, 7 are exposed to a thermal stress despite the heat-resistant film 5, a cooling using Peltier elements combined with air cooling is possible.

The gas in which the fine dust particles are to be measured can flow unhindered through the pipe 1. To carry out the measurement, approximately 100 to 200 pulses (e.g., with a varying pulse length and/or a varying pulse repetition rate) are emitted by a laser source with a wavelength. An average is made with the signal. To determine the size distribution of the fine dust particles, the pulse lengths are varied from 1 $\mu$S to 100 $\mu$S. In the case of the pulse repetition rate, a variation of 1 kHz to 50 kHz is provided. By measuring with three different wavelengths from the laser source, for instance 400 nm, 700 nm and 1000 nm, it is possible to make a better differentiation between fine dust particles and other absorbing materials.

Since sound waves propagate more quickly in the direction of flow than against the direction of flow, the flow rate of the gas flowing through can also be determined from the different propagation times of the sound signal. In order to be able to make inferences about the emissions caused in the case of a measurement in the exhaust gas, it is not sufficient to determine only the concentration in the exhaust gas; it is also necessary to determine the volume emitted in the unit of time. To do this, the measurement of the speed of the outflowing gas is necessary.

LIST OF REFERENCE NUMBERS

1 Pipe
2 Planar mirror
3 Line of light incidence points
4 Concave mirror
5 Film
6 Ultrasonic sensor
7 Optical detector
8 Annular housing

The invention claimed is:
1. A photoacoustic detector for measuring a concentration of fine dust particles in gas, the detector comprising:
    at least one acoustic sensor for detecting an acoustic signal;
    a pulsed light source for providing excitation light having a configurable pulse length and a configurable pulse rep- etition rate, wherein by changing the pulse length and/or the pulse repetition rate, a size distribution of the fine dust particles can be determined; and a comparison system configured to compare a plurality of photoacoustic signals generated with different pulse lengths and/or different pulse repetition rates to determine the size distribution of the particles.

2. The photoacoustic detector according to claim 1, wherein the photoacoustic detector is configured to measure a concentration of carbon particles.

3. The photoacoustic detector according to claim 1, further comprising an optical sensor configured to detect the excitation light scattered by the fine dust particles.

4. The photoacoustic detector according to claim 3, wherein one of the at least one acoustic sensor and one of the at least one optical sensor are arranged in close proximity to each other and in a region of a maximum signal of a common concentration of the acoustic signal and of the excitation light scattered by the fine dust particles.

5. The photoacoustic detector according to claim 1, further comprising an arrangement for concentrating acoustic energy in an area of the detector in which a temperature is lower than a temperature of the gas containing the fine dust particles.

6. The photoacoustic detector according to claim 5, wherein the arrangement for the concentrating of the acoustic energy comprises reflectors, which reflectors also are configured for concentrating of the excitation light scattered by the fine dust particles.

7. The photoacoustic detector according to claim 1, wherein the detector is configured to measure fine dust particles directly in hot gas flowing through the detector.

8. The photoacoustic detector according to claim 1, wherein the at least one acoustic sensor for detecting an acoustic signal comprises at least one sound pressure sensor, the detector further comprising:
at least one scattered light sensor; and
a cooling device provided for the at least one sound pressure sensor and/or the at least one scattered light sensor.

9. The photoacoustic detector according to claim 1, further comprising a thermal decoupling arranged between a region of production of an acoustic signal and a region of detection of the acoustic signal.

10. The photoacoustic detector according to claim 9, wherein the thermal decoupling comprises a thermally insulating sound-permeable and/or transparent film.

11. The photoacoustic detector according to claim 1, wherein the at least one acoustic sensor for detecting the acoustic signal comprises at least one optical microphone.

12. The photoacoustic detector according to claim 1, wherein the pulsed light source comprises at least three diode lasers for providing the excitation light.

13. The photoacoustic detector according to claim 1, further comprising a measuring area, wherein the detector is configured and arranged to guide the excitation light multiple times through the measuring area.

14. The photoacoustic detector according to claim 1, further comprising a cylindrical acoustic resonator having a cylinder oscillation,
wherein the cylindrical acoustic resonator includes an arrangement to guide the excitation light such that a sound wave produced by absorption of the excitation light is a second azimuthal resonance of the cylinder oscillation.

15. The photoacoustic detector according to claim 1, further comprising:
a housing;
an acoustically open measuring range that is not completely surrounded by the housing;
an arrangement for introducing the excitation light into the measuring range so that the excitation light is absorbed by the fine dust particles located in the measuring range to produce acoustic energy; and
a concentrating arrangement providing a local maximum of sound pressure of the acoustic energy at least one position, wherein the at least one acoustic sensor is arranged in a vicinity of the at least one position.

16. A measuring device configured for measuring exhaust gases of a motor vehicle or an engine test bench comprising the photoacoustic detector according to claim 1.

17. A photoacoustic detector for measuring a concentration of fine dust particles in gas, the detector comprising:
at least one acoustic sensor for detecting an acoustic signal;
a pulsed light source for providing excitation light having a configurable pulse length and a configurable pulse repetition rate, wherein by changing the pulse length and/or the pulse repetition rate, a size distribution of the fine dust particles can be determined; and
a cylindrical acoustic resonator having a cylinder oscillation, wherein the cylindrical acoustic resonator includes an arrangement to guide the excitation light such that a sound wave produced by absorption of the excitation light is a second azimuthal resonance of the cylinder oscillation, and
wherein the arrangement to guide the excitation light comprises four mirrors arranged oppositely in groups of respectively two mirrors in the cylindrical acoustic resonator.

18. The photoacoustic detector according to claim 17, wherein the concentrating arrangement comprises acoustic mirrors.

19. The photoacoustic detector according to claim 18, wherein the acoustic mirrors comprise parabolic acoustic mirrors.

20. A method for a photoacoustic measurement of fine dust particles in gas, comprising:
supplying excitation light with a pulsed light source;
detecting at least one photoacoustic signal;
varying at least one of a pulse length and a pulse repetition rate of the excitation light, and detecting at least one second photoacoustic signal; and
determining the photoacoustic measurement based on the at least one photoacoustic signal and the at least one second photoacoustic signal by comparing the at least one photoacoustic signal with the at least one second photoacoustic signal generated with different pulse lengths and/or different pulse repetition rates to determine a size distribution of the particles.

* * * * *